(12) United States Patent
Bokerman et al.

(10) Patent No.: US 8,048,384 B1
(45) Date of Patent: Nov. 1, 2011

(54) CHEMOCHROMIC HYDROGEN SENSORS

(75) Inventors: Gary Bokerman, Rapid City, MI (US); Ali Tabatabaie-Raissi, Melbourne, FL (US); Nazim Muradov, Melbourne, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 12/872,090

(22) Filed: Aug. 31, 2010

(51) Int. Cl.
G01N 21/75 (2006.01)
G01N 31/22 (2006.01)
G01N 33/52 (2006.01)
G01N 21/76 (2006.01)
G01N 7/00 (2006.01)
G01N 33/497 (2006.01)

(52) U.S. Cl. ........ 422/400; 422/52; 73/31.05; 73/31.06; 73/23.2

(58) Field of Classification Search .................. None
See application file for complete search history.

(56) References Cited

U.S. PATENT DOCUMENTS

| | | | |
|---|---|---|---|
| 5,849,073 A | 12/1998 | Sakamoto et al. | |
| 6,895,805 B2 * | 5/2005 | Hoagland | 73/31.06 |
| 7,897,057 B1 * | 3/2011 | O'Connor et al. | 216/24 |
| 2004/0037740 A1 * | 2/2004 | Liu et al. | 422/58 |
| 2004/0115818 A1 | 6/2004 | Puri et al. | |
| 2006/0240245 A1 * | 10/2006 | Ishida et al. | 428/312.6 |
| 2007/0042906 A1 * | 2/2007 | Pitts et al. | 502/350 |
| 2007/0224081 A1 * | 9/2007 | Bokerman et al. | 422/56 |
| 2010/0098593 A1 * | 4/2010 | Trakhtenberg et al. | 422/98 |

* cited by examiner

Primary Examiner — Brian J Sines
Assistant Examiner — Jennifer Wecker
(74) Attorney, Agent, or Firm — Jetter & Associates, P.A.

(57) ABSTRACT

A chemochromic $H_2$ sensor includes supports including a plurality of metal oxide particles exclusive of titania, and a platinum group metal (PGM) compound on the supports. The PGM compound is an oxide, hydroxide hydrated oxide, PGM salt or a PGM complex. When the PGM compound is a PGM salt or a PGM complex, the supports can include titania particles.

11 Claims, 3 Drawing Sheets

Table 1. Pigment preparation matrix

| Batch ID | Pigment (Pd Compound/Support) + Accelerant (Mo Compound) | Weight of Pigment, g | Pd in Pigment, g-mol | Refer to Example # | Weight of Hyd Ammonium Molybdate^, g | Accelerant Mo Content, g-mol | Mo/Pd Atomic Ratio | Weight of RTV 3145, g | Pigment Concentration in Silicone, % |
|---|---|---|---|---|---|---|---|---|---|
| SR-1-5H | PdO/TiO₂ (Aldrich) | 0.2988 | 8.1E-05 | 1 | none | none | 0.0 | 9.997 | 3 |
| SR-1-5K | PdO/SrTiO₃ (Aldrich) | 0.2994 | 8.2E-05 | 2 | none | none | 0.0 | 9.9993 | 3 |
| SR-1-5S | PdO/SrZrO₃ (Aldrich) | 0.2998 | 8.2E-05 | 5 | none | none | 0.0 | 10.0005 | 3 |
| SR-1-5U | PdO/TiO₂ (Aldrich) | 0.5995 | 0.00016 | 1 | none | none | 0.0 | 9.9997 | 6 |
| SR-1-5V | PdO/SrTiO₃ (Aldrich) | 0.5996 | 0.00016 | 2 | none | none | 0.0 | 9.9999 | 6 |
| SR-1-5Z | PdO/SrZrO₃ (Aldrich) | 0.5998 | 0.00016 | 5 | none | none | 0.0 | 9.9998 | 6 |
| SR-1-6A | PdO/SrTiO₃ + Ammonium Molybdate (AM) | 0.6009 | 0.00017 | 2 & 11 | 0.2549 | 0.00144377 | 8.6 | 10.0012 | 6 |
| SR-1-6B | PdO/SrZrO₃ + AM | 0.5982 | 0.00016 | 5 & 11 | 0.2544 | 0.00144094 | 8.8 | 9.9998 | 6 |
| SR-1-6C | PdO/SrZrO₃ + AM | 0.5978 | 0.00016 | 5 & 11 | 0.0292 | 0.00016539 | 1.0 | 9.9982 | 6 |
| SR-1-6D | PdO/SrTiO₃ (Aldrich) + AM | 0.6002 | 0.00017 | 2 & 11 | 0.0299 | 0.00016936 | 1.0 | 9.9994 | 6 |
| SR-1-6E | Pd(OCOCH₃)₂/TiO₂ | 0.5993 | 0.00017 | 5 & 11 | 0.0899 | 0.00050924 | 3.1 | 9.9977 | 6 |
| SR-1-6F | Pd(OCOCH₃)₂/TiO₂ (F) | 0.5036 | 2.9E-05 | 6 | none | none | 0.0 | 3.0034 | 16.7 |
| SR-1-6G | Pd(OCOCH₃)₂/+MoO₃ | 0.4995 | 2.3E-05 | 9 | none | 0.00114151 | 39.0 | 3.0047 | 16.7 |
| SR-1-6H | PdO/SrTiO₃ (Aldrich) + AM | 0.3008 | 8.2E-05 | 2 & 11 | 0.0475 | 0.000269304 | 3.3 | 4.9984 | 6 |
| SR-1-6I | PdO/SrZrO₃ + AM | 0.3 | 8.2E-05 | 2 & 11 | 0.0662 | 0.000377496 | 4.6 | 4.9999 | 6 |
| SR-1-6K | PdO/SrZrO₃ + AM | 0.2999 | 8.2E-05 | 5 & 11 | 0.0665 | 0.000377666 | 4.6 | 5.0001 | 6 |
| SR-1-6M | Pd(OCOCH₃)₂/ZrO₂ * | 0.5005 | 0.00011 | 8 | none | none | 0.0 | 2.9996 | 16.7 |
| SR-1-6L | No pigment — only molybdenum anhydride as support | 0.5002 | none | 12 | none | 0.00034725 | — | 2.9968 | none |
| SR-1-6N | Pd(OCOCH₃)₂/TiO₂ | 0.4998 | 0.0001 | 7 | none | none | 0.0 | 2.9998 | 16.7 |

* Stanford Material OX 40 3N5F zirconia.
^ Hydrated ammonium molybdate, $(NH_4)_6Mo_7O_{24}\cdot 4H_2O$.

*FIG. 3*

CHEMOCHROMIC HYDROGEN SENSORS

FIELD

Disclosed embodiments relate to chemochromic-based hydrogen sensors.

BACKGROUND

One of the future alternatives to current fossil-based transportation fuels has been centered on hydrogen gas ($H_2$). Currently, $H_2$ is the primary energy source of today's space exploration projects (e.g., as rocket propellant). It is also used in fuel cells that power a variety of machinery including automobiles. Furthermore, $H_2$ is an important industrial commodity produced and used in many industries. For example, it is used for the reduction of metal oxides (e.g. iron ore), ammonia synthesis, and production of hydrochloric acid, methanol and higher alcohols, aldehydes, hydrogenation of various petroleum, coal, oil shale and edible oils, among others. However, $H_2$ is a colorless, odorless gas, and is also a flammable gas with a lower explosive limit of about 4% in air. Therefore reliable $H_2$ sensors are required to detect $H_2$ leaks wherever $H_2$ is produced, stored, or used.

To detect $H_2$, sensors comprising a palladium alloy Schottky diode formed on a silicon substrate are known. These sensors are based on metal-oxide-semiconductor (MOS) technology that is used in the semiconductor industry. The gas sensing MOS structures comprise a $H_2$-sensitive metal (palladium or its alloy) on a dielectric (e.g., an oxide) adherent to a semiconductor. This $H_2$ sensor has been commercialized and exploited for detecting $H_2$ leaks during pre-launches of space vehicles. Others have also used palladium or the like as a sensing element for detecting $H_2$. A $H_2$ sensor containing an array of micromachined cantilever beams coated with palladium/nickel has also been disclosed.

Semiconductors with wide band-gap (e.g. gallium nitride) have also been used to make diodes for $H_2$ detection. One of the concerns for all of these types of sensors using palladium or the like is the requirement of a high operating temperature (greater than 200° C.) and further elevated temperatures (greater than 500° C.) to reactivate the sensing element, bringing about lengthy analysis. Another issue is sensitivity of the sensing element to unintended compounds that are commonly found in the atmosphere, including water vapor, various hydrocarbons, and various reducing gases such as carbon monoxide and hydrogen sulfide.

Although not conventionally used, chemochromic $H_2$ sensors are known. Some chemochromic $H_2$ sensors lack field stability and have a tendency to crack and peel and some can be washed off by precipitation and/or condensation. Moreover, some chemochromic $H_2$ sensors do not show selectivity to $H_2$. Thus, there remains a need for an improved, reliable and durable chemochromic $H_2$ sensor for a variety of applications, including space, transportation, oil refineries, and chemical plants.

BRIEF DESCRIPTION OF THE DRAWINGS

FIG. 3 is a table that provides a chemochromic $H_2$ sensor preparation matrix for a plurality of different embodiments of the invention.

DETAILED DESCRIPTION

Figure 1:
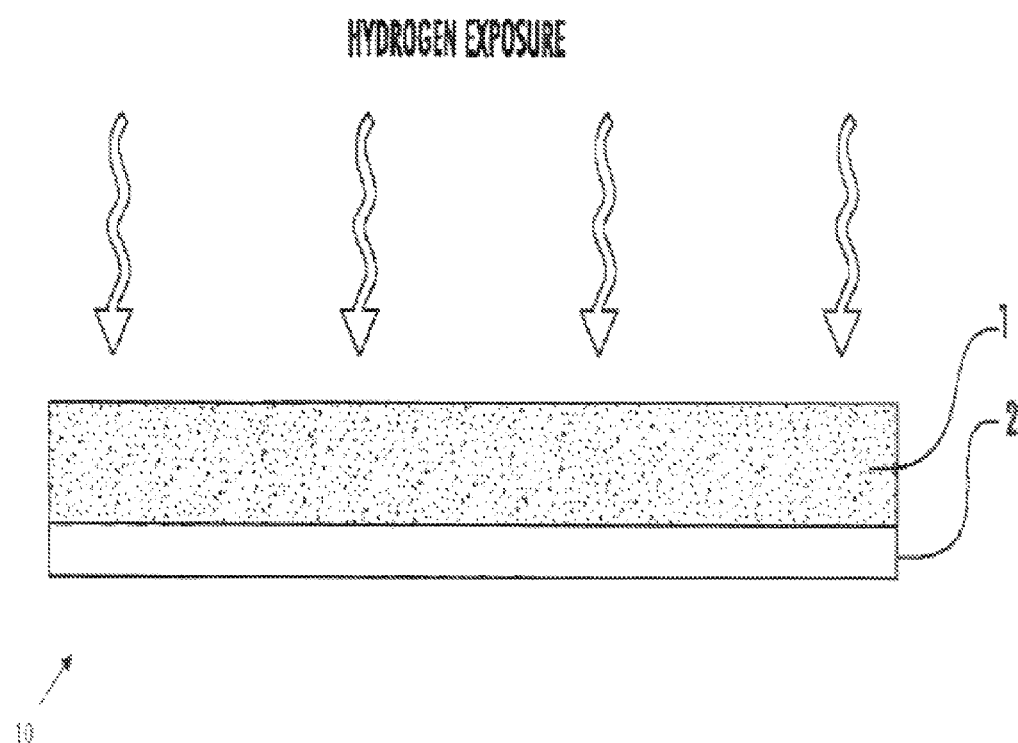
FIG. 1 is a depiction of an exemplary two layer $H_2$ sensor comprising a composite layer including supports comprising a plurality of metal oxide particles and a PGM compound on the supports, and a gas permeable polymer that forms a continuous phase that completely encapsulates both the supports and the PGM compound which are both embedded in the polymer, according to an embodiment of the invention.

Disclosed embodiments in $t_{hi}s$ Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

This Disclosure includes new chemochromic $H_2$ sensors comprising supports including a plurality of metal oxide particles and a PGM compound that functions as a $H_2$ sensitive pigment on the supports. The Inventors have discovered sensitive, reliable, and durable chemochromic $H_2$ sensors can utilize a wide variety of supports including support materials other than titania, and the PGM compounds can include PGM salts or PGM complexes. In one embodiment, the chemochromic $H_2$ sensor comprises supports comprising a plurality of metal oxide particles exclusive of titania, and a PGM compound on the supports. In another embodiment, the chemochromic $H_2$ sensor comprises supports comprising a plurality of metal oxide particles, and a PGM salt or a PGM complex on the supports.

Typically the supports comprise metal oxides, mixed metal oxides, and their salts that are colorless, white, or slightly colored. The metal oxides, mixed metal oxides and their salts can comprise at least one transition metal, such as titanium, zirconium and cerium (e.g., embodied as $CeO_2$). In one embodiment the supports comprise a plurality of Group IV metal oxide particles, such as $ZrO_2$, $SrTiO_3$, or $SrZrO_3$ particles. In one embodiment the particle size for the support particles is in a range from 0.1 to 1.0 μm, and in one particular embodiment, from 0.2 to 0.25 μm to maximize opacity.

The PGM for the PGM compound can comprise one or more of palladium, iridium, ruthenium, platinum, rhodium, gold, and silver. The PGM compounds generally comprise PGM oxides, hydroxides, and hydrated oxides. In certain embodiments the PGM compounds comprise PGM salts (e.g., acetates, or other carboxylates such as propionates), or PGM complexes such as acetylacetonates, dichlorodiamine, tetraamine, and tetrachloropalladate.

The PGM salt can be an organic salt or an inorganic salt. In one particular embodiment the PGM salt comprises a carboxylate, such as palladium acetate, $Pd(OCOCH_3)_2$, or other carboxylates such as propionates. Exemplary inorganic salt examples include chlorides, sulfates, and iodide-based salts.

Using a PGM salt or PGM complex instead of a conventional PGM compound such as a PGM oxide, hydroxide, or hydrated oxide for the pigment can allow significant simplification in $H_2$ sensor preparation. The $H_2$ sensor preparation method using a PGM salt or PGM complex can be simplified because PGM salts or PGM complexes can be dissolved in a suitable solvent to form a PGM solution which can then be added to a slurry solution comprising support particles, followed by drying of the resulting solution. Accordingly, the neutralization and filtration stages generally needed when using conventional PGM compounds (e.g., PGM oxides, hydroxides, hydrated oxides) to form $H_2$ sensors are effectively eliminated. When the PGM salt or PGM complex has low solubility in water, such as the organic PGM salt palladium acetate, solvents such as weak organic acids (e.g., acetic acid) may be used.

The $H_2$ sensor can further comprise an accelerant or contrast additive. For example, the accelerant or contrast additive can comprise $MoO_3$, $(NH_4)_6Mo_7O_{24}$, or polyoxometalates that include V, Nb, Ta, Cr, Mo or W.

One embodiment (a) comprises adding a PGM salt or PGM complex to a slurry of support particles comprising metal oxide particles exclusive of titania, and then neutralizing the resulting mixture by adding an alkali or an acid, as required. In another embodiment (b), PGM salts or PGM complexes are added to an alkali or an acid, as needed, to a slurry of the support particles comprising metal oxide particles exclusive of titania, while maintaining the pH of the slurry from 3 to 11, such as from 6 to 11, and in the particular case mineral acid salts of the PGM are used, from 8 to 11, to neutralize the mixture. In yet another embodiment (c), a slurry of the support particles comprising metal oxide particles exclusive of titania is premixed with a higher amount of an alkali or an acid, as required, than required to neutralize the PGM salts or PGM complex, and then a PGM salt or PGM complex is added to neutralize. Embodiment (b) generally allows the fine PGM compounds to be present more uniformly on the surfaces of the support particles with a lower amount of the PGM compounds needed to be used. The alkalis for neutralization, if needed, can include sodium hydroxide, potassium hydroxide, sodium carbonate, and ammonia, for example. The acids for neutralization, if needed, can include hydrochloric acid, sulfuric acid, nitric acid, and acetic acid. The temperature for the neutralization reaction can be in the range of 50° C. to 90° C.

The PGM compounds can be applied in an amount of 0.5 to 10% by weight, such as 1 to 5% by weight as expressed by the PGM based on the weight of the supports. The Inventors have recognized that an amount of PGM compound lower than 0.5% by weight may cause insufficient color change to detect gas leakage, while an amount of higher than 10% by weight can become uneconomical with no further improvement in the sensing function being expected.

The effectiveness of the $H_2$ gas sensors, such as $H_2$ sensors disclosed herein, is typically evaluated by measuring the time necessary to reach a given level of color change, and by determining the total amount of color change. The latter is expressed as $\Delta E$ and is measured by a colorimeter. $\Delta E$ measures a difference in color by measuring specific parameters of the film (L, a, b). These parameters refer to a color system for measuring absolute chromaticity, L*a*b* and color difference $\Delta(L^*a^*b^*)$ or $\Delta E$. Color is defined in three dimensions: hue, chroma (saturation) and lightness. L*=gradient from light to dark, a*=gradient from red to green, and b*=gradient from yellow to blue, and $\Delta E^* = \{(\Delta L^*)^2 + (\Delta a^*)^2 + (\Delta b^*)^2\}^{1/2}$. This equation gives a standard measurement technique by which one can compare color changes from different chemochromic $H_2$ sensor film samples. The greater the $\Delta E^*$ value, the greater the color contrast. Chemochromic $H_2$ sensor films can be analyzed both before and after exposure to $H_2$, allowing quantification of the intensity of the color change.

In one embodiment, a disclosed $H_2$ sensor includes a moisture-cured silicone polymer that forms a continuous/matrix phase that completely encapsulates the PGM compound and supports in a specified ratio to give a composition that responds in a controllable way to the presence of $H_2$. In this embodiment, the PGM compound, support particles and optional accelerant is generally 1 to 50 wt. % of the overall $H_2$ sensor, and is 2-20 wt. % in one embodiment. Upon evaluating a series of alternate supports for the chemochromic $H_2$ sensor including a silicone matrix, all, with the exception of those with very small particle size supports, gave $\Delta E^*$ values equal or better to those of known $PdO/TiO_2$ chemochromic $H_2$ sensors as described below relative to FIG. 2.

FIG. 1 is a depiction of an exemplary two layer $H_2$ sensor 10 according to an embodiment of the invention. $H_2$ sensor 10 comprises a composite layer 1 including supports comprising a plurality of metal oxide particles and a PGM compound on the supports, and a gas permeable polymer that forms a continuous phase that completely encapsulates both the supports and the PGM compound which are both embedded in the polymer. An optional clear silicone layer 2 is also shown. The clear silicone layer 2 does not generally include any PGM compound.

An example of the impact of support particle size on chemochromic $H_2$ sensor performance is demonstrated with samples containing $ZrO_2$. The particle size of $ZrO_2$ is much less than the value of approximately 0.22 microns which the Inventors have found generally maximizes the opacity or hiding power of a chemochromic pigment. In this example, the resulting sample was translucent although the chemochromic color change was observable with $H_2$ exposure. Such a chemochromic $H_2$ sensor system can be an advantage since the events occurring behind the chemochromic system can be observed. With silicone chemochromic tapes the overcoat system developed for $H_2$ from behind an observer can be eliminated since the initial color change is readily apparent.

As described above, another disclosed embodiment comprises the addition of an accelerant to give color change rates comparable with $Pd/TiO_2$ systems. In this embodiment, the $H_2$ sensor further comprises an accelerant or contrast additive mixed with the PGM compound selected from $MoO_3$, $(NH_4)_6Mo_7O_{24}$, and polyoxometalates that include V, Nb, Ta, Cr, Mo, and W. When the level of accelerant is optimized, the rate of color change can be increased by a factor of 2-5, and modest increases in $\Delta E^*$ values are also observed.

EXAMPLES

Disclosed embodiments are further illustrated by the following specific Examples, which should not be construed as limiting the scope or content of this Disclosure in any way.

Figure 2:
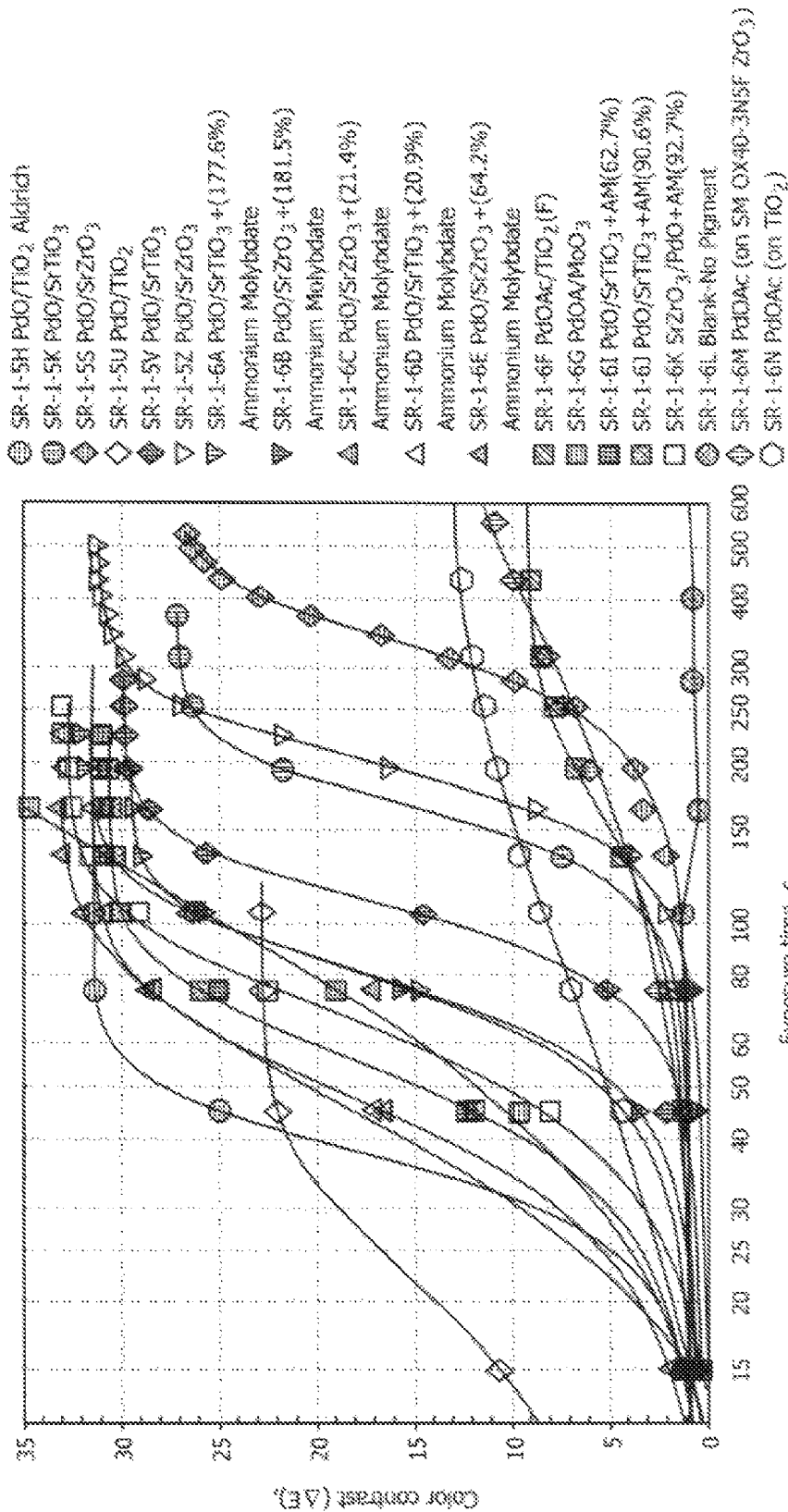
FIG. 2 is color contrast vs. exposure time data for a variety of chemochromic $H_2$ sensors, according to various embodiments of the invention.

The H$_2$ sensor preparation matrix is shown as Table 1 in FIG. 3 for the Examples described below. Data from the H$_2$ exposure tests performed as described in the Examples is shown in FIG. 2.

Chemochromic H$_2$ sensors to be tested were tape casted. The tape-casting process included weighing out the pigment powder that is a mixture of metal oxide support particles and PGM compound(s), RTV 3145 silicone, and ammonium molybdate ((NH$_4$)$_6$Mo$_7$O$_{24}$) if used as an accelerant or contrast additive. The PGM compound mixed with a metal oxide support, (and optionally ammonium molybdate) were grinded in a mortar, and admixed with the RTV 3145 silicone. This mixture was then scraped up and applied to a flat piece of taped-down wax paper. A doctor blade was used to slowly draw out the silicone-pigment paste into a thin film. The film thickness of the samples prepared was typically 10 mils.

After letting the sheets cure overnight, the sheets were cut into sample sheets for the H$_2$ exposure tests. Each sample was cut into a 1⅜ inch by 1⅜ inch square. The wax paper was allowed to remain on the back side of each sample during the tests, due to the thinness of the sheet and its saran-wrap like tendency to stick together. Before testing, each sample was marked with a small cut near its upper left-hand corner, and then subjected to colorimetric measurements using a Konica-Minolta CR-10 instrument that gave the $\Delta L^*$, $\Delta a^*$, and $\Delta b^*$ values at five locations on the sample sheet—each of its four corners, and in the middle. The sample was then placed (exposed side of membrane down) onto a badge-holder. H$_2$ produced by a H$_2$ generator was passed through a narrow tube into the bottom of the badge-holder. Samples were placed onto the badge-holder, and then capped at the top.

A shut-off valve was used to ensure a consistent and immediate exposure to the H$_2$ flow. Before each test, the H$_2$ flow was allowed to stabilize before switching to flow into the badge sample holder. Each sample was exposed to H$_2$ for a set length of time, and then taken out of the badge-holder and extent of color change measured by the Konica-Minolta CR-10 instrument at five locations on the sample sheet. This process repeated for as long as the sample color change was measurable. Collective testing times ranged from a few minutes to well over an hour, based on the kinetics of coloration.

Example 1

Reference PdO/TiO$_2$ H$_2$ Sensor; Related Art

As a basis for comparison to disclosed embodiments, a chemochromic H$_2$ sensor comprising PdO particles deposited on TiO$_2$ support particles was prepared. In a beaker, 50 mL of deionized (DI) water and 5.0 g of Aldrich TiO$_2$ sample were mixed. With a magnetic stir bar, the mixture was continuously stirred for one hour then heated to a temperature of 70° C. In a separate beaker, 10 mL of DI water, 0.25 g of PdCl$_2$, and 2.5 mL of concentrated HCl were mixed. The PdCl$_2$ solution was slowly added to the support solution, carefully. Saturated NaOH solution was used to maintain the pH at levels between 10 and 11. Once all of the PdCl$_2$ had been combined with the support, the pH of the solution was lowered to 8 using concentrated HCl while allowing the stirring to continue at 70° C. for one hour. After one hour, heating was stopped and the solution was filtered. The residue was washed with DI water several times and placed in an oven, set at 100° C., until dry. Once dry, the PdO/TiO$_2$ chemochromic pigment sample was crushed into a powder and stored in a glass vial.

Example 2

PdO/SrTiO$_3$ H$_2$ Sensor According to an Embodiment of the Invention

In a beaker, 50 mL of de-ionized (DI) water and 5.0 g of Aldrich SrTiO$_3$ sample were mixed. With a magnetic stir bar, the mixture was continuously stirred for one hour, and then heated to a temperature of 70° C. In a separate beaker, 10 mL of DI water, 0.25 g of PdCl$_2$, and 2.5 mL of concentrated HCl were mixed. The PdCl$_2$ solution was slowly added to the support solution, carefully. Saturated NaOH solution was used to maintain the pH at levels between 10 and 11. Once all of the PdCl$_2$ had been combined with the support particles, the pH of the solution was lowered to 8 using concentrated HCl and allowing the stirring to continue at 70° C. for one hour. After one hour, heating was stopped and the solution was filtered. The residue was washed with DI water several times and placed in an oven, set at 100° C., until dry. Once dry, the PdO/SrTiO$_3$ chemochromic H$_2$ sensor sample was crushed into a powder and stored in a glass vial.

Example 3

PdO/ZrO$_2$ H$_2$ Sensor According to an Embodiment of the Invention

In a beaker, 50 mL of de-ionized (DI) water and 5.0 g of Fisher ZrO$_2$ sample were mixed. With a magnetic stir bar, the mixture was continuously stirred for one hour then heated to a temperature of 70° C. In a separate beaker, 10 mL of DI water, 0.25 g of PdCl$_2$, and 2.5 mL of concentrated HCl were mixed. The PdCl$_2$ solution was slowly added to the support solution, carefully. Saturated NaOH solution was used to maintain the pH at levels between 10 and 11. Once all of the PdCl$_2$ had been combined with the support particles, the pH of the solution was lowered to 8 using concentrated HCl and allowing the stifling to continue at 70° C. for one hour. After one hour, heating was stopped and the solution was filtered. The residue was washed with DI water several times and placed in an oven, set at 100° C., until dry. Once dry, the PdO/ZrO$_2$ chemochromic H$_2$ sensor sample was crushed into a powder and stored in a glass vial.

Example 4

PdO/CeO$_2$ H$_2$ Sensor According to an Embodiment of the Invention

In a beaker, 50 mL of de-ionized (DI) water and 6.8 g of Aldrich CeO$_2$ sample were mixed. With a magnetic stir bar, the mixture was continuously stirred for one hour then heated to a temperature of 70° C. In a separate beaker, 10 mL of DI water, 0.25 g of PdCl$_2$, and 2.5 mL of concentrated HCl were mixed. The PdCl$_2$ solution was slowly added to the support solution, carefully. Saturated NaOH solution was used to maintain the pH at levels between 10 and 11. Once all of the PdCl$_2$ had been combined with the support particles, the pH of the solution was lowered to 8 using concentrated HCl and allowing the stirring to continue at 70° C. for one hour. After one hour, heating was stopped and the solution was filtered. The residue was washed with DI water several times and placed in an oven, set at 100° C., until dry. Once dry, the PdO/CeO$_2$ sample was crushed into a powder and stored in a glass vial.

Example 5

PdO/SrZrO$_3$ H$_2$ Sensor According to an Embodiment of the Invention

In a beaker, 50 mL of de-ionized (DI) water and 5.0 g of Aldrich SrZrO$_3$ sample were mixed. With a magnetic stir bar, the mixture was continuously stirred for one hour then heated to a temperature of 70° C. In a separate beaker, 10 mL of DI water, 0.25 g of PdCl$_2$, and 2.5 mL of concentrated HCl were mixed. The PdCl$_2$ solution was slowly added to the support solution, carefully. Saturated NaOH solution was used to maintain the pH at levels between 10 and 11. Once all of the PdCl$_2$ had been combined with the support particles, the pH of the solution was lowered to 8 using concentrated HCl and allowing the stirring to continue at 70° C. for one hour. After one hour, heating was stopped and the solution was filtered. The residue was washed with DI water several times and placed in an oven, set at 100° C., until dry. Once dry, the PdO/SrZrO$_3$ sample was crushed into a powder and stored in a glass vial.

Example 6

Pd Organic Salt/TiO$_2$ H$_2$ Sensor Formed Using a Pd Organic Salt According to an Embodiment of the Invention 0.2 g of Pd(OCOCH$_3$)$_2$ was dissolved in 10 mL of glacial acetic acid at 70° C. 2 mL of the resulting solution was added to 3 g of TiO$_2$ (Aldrich) powder and the slurry was carefully mixed and left overnight to dry.

Example 7

Pd Organic Salt/TiO$_2$ H$_2$ Sensor Formed Using a Pd Organic Salt According to an Embodiment of the Invention 0.12 g of Pd(OCOCH$_3$)$_2$ was dissolved in 10 mL of glacial acetic acid at 70° C. The resulting solution was added to 2.5 g of TiO$_2$ (Aldrich) powder and the slurry was carefully mixed and left overnight to dry.

Example 8

Pd Organic Salt/ZrO$_2$ H$_2$ Sensor Formed Using a Pd Organic Salt According to an Embodiment of the Invention 0.12 g of Pd(OCOCH$_3$)$_2$ was dissolved in 10 mL of glacial acetic acid at 70° C. The resulting solution was added to 2.5 g of ZrO$_2$ powder and the slurry was carefully mixed and left overnight to dry.

Example 9

Pd Organic Salt/MoO$_3$ H$_2$ Sensor Formed Using a PGM Organic Salt According to an Embodiment of the Invention 0.2 g of Pd(OCOCH$_3$)$_2$ was dissolved in 10 mL of glacial acetic acid at 70° C. 2 mL of the resulting solution was added to 3 g of molybdenum anhydride (MoO$_3$) and the slurry was carefully mixed and left overnight to dry.

Example 10

H$_2$ Sensors Including Silicone for Complete Encapsulation 0.3-0.6 g of selected H$_2$ sensor powder as prepared in Examples 1-9 was manually admixed with enough moisture curing silicone sealant (Dow Corning R 3145 RTV Adhesive/Sealant-Clear) to give 3-10 g total (see Table 1 in FIG. 3, samples SR-1-5H to SR-1-6G). The uncured H$_2$ sensor powder/sealant was used to prepare a rubber sheet indicator. A flat piece of wax paper was placed on top of the lab bench onto which the uncured pigment/sealant was spread using a draw down blade so that a uniform sheet of material was deposited ready for curing. After 24-48 hours, a thin rubbery sheet was removed with wax paper still attached to the film. Cut up pieces of this wax paper back sheet were used as a hydrogen indicator tapes by exposing them to hydrogen gas. After the time indicated in FIG. 2 with exposure to hydrogen gas, the original white-to-beige color of the cured compound changed to gray. Upon removal from hydrogen chamber, the gray color remained.

Example 11

H$_2$ Sensors Including Accelerants

In an experiment to demonstrate accelerant action, MoO$_3$ or (NH$_4$)$_6$Mo$_7$O$_{24}$ was added to H$_2$ sensors according to embodiments of the invention in levels varying from 1 to as much as 40 metal ion equivalent per PGM (e.g., Pd) atom content of the H$_2$ sensor which gave a chemochromic H$_2$ sensor that showed a visually darker color upon contact with H$_2$ than without the molybdenum complex and/or oxide. In addition, the extent and rate of color change was also found to significantly increase compared to that without the molybdenum complex and/or oxide as demonstrated in FIG. 2.

Example 12

Encapsulated PdO/MoO$_3$ H$_2$ Sensor 0.5 g of selected Pd organic salt/MoO$_3$ H$_2$ sensor powder as described above in the Example 9 was manually admixed with enough moisture curing silicone sealant (Dow Corning R 3145 RTV Adhesive/Sealant-Clear) to give 3 g total (see Table 1, samples SR-1-6I-K and SR-1-6L-N). The uncured pigment/sealant was used to prepare a rubber sheet indicator. A flat piece of wax paper was placed on top of the lab bench onto which the uncured pigment/sealant was spread using a draw down blade so that a uniform sheet of material was deposited ready for curing. After 24-48 hrs, a thin rubbery sheet was removed with wax paper still attached to the film. Cut up pieces of this wax paper back sheet were used as a hydrogen indicator tapes by exposing them to hydrogen gas. After the time indicated in FIG. 2 with exposure to hydrogen gas, the original white-to-beige color of the cured compound changed to gray. Upon removal from H$_2$ chamber, the gray color remained.

Note that in this Example, the color intensity far exceeds that of other samples. This is likely due to the additional chemochromic effect provided by the molybdenum anhydride (MoO$_3$) support. It is known that upon exposure to H$_2$, MoO$_3$ is transformed into its reduced blue-colored form (MoO$_{3-x}$). However, this process is very slow (as the blank (i.e., no pigment) batch that includes only MoO$_3$ as the support clearly shows in FIG. 2). The presence of Pd organic salt is believed to provide the auto-catalytic effect and significantly accelerates the reduction of $MoO_3$ to its reduced form. On the other hand, the reduced form of Mo-oxide promotes further transformation of Pd organic salt to metallic Pd. The combined effect results in an almost pitch black coloration of the Pd/$MoO_3$ $H_2$ sensor. It should be noted, however, that after prolonged period of time (days) some bleaching effect of the pigment is possible due to oxidation of the reduced form of Mo-oxide to its original oxidized form. This effect however, does not alter the coloration achieved due to reduction of Pd organic salt to metallic Pd.

Example 13

Color Contrast Inside a RTV Matrix

Color contrast measurements, $\Delta E^*$, of the $H_2$ sensors were conducted inside a RTV matrix with a pigment to matrix ratio of 3 (or 6) to 100 (film). The samples' colorimetric parameters $a^*$, $b^*$, and $L^*$ were measured before and after exposure to 100% $H_2$ gas and $\Delta E^*$ values were determined. Results are shown in FIG. 2

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

We claim:

1. A chemochromic $H_2$ sensor, comprising:
   supports comprising a plurality of metal oxide particles exclusive of titania, and
   a platinum group metal (PGM) compound on said supports, said PGM compound comprising an oxide, hydroxide, hydrated oxide, PGM salt or PGM complex, wherein said chemochromic $H_2$ sensor is an irreversible color changing sensor that changes color in a presence of $H_2$.

2. The chemochromic $H_2$ sensor of claim 1, wherein said plurality of metal oxide particles comprise transition metal oxide particles.

3. The chemochromic $H_2$ sensor of claim 2, wherein said transition metal oxide particles comprise Group IV metal oxide particles.

4. The chemochromic $H_2$ sensor of claim 3, wherein said Group IV metal oxide particles comprise $ZrO_2$, $SrTiO_3$ or $SrZrO_3$.

5. The chemochromic $H_2$ sensor of claim 1, wherein a PGM in said PGM compound comprises palladium, iridium, ruthenium, platinum, rhodium, gold or silver.

6. The chemochromic $H_2$ sensor of claim 1, wherein said PGM compound comprises said PGM salt, and wherein said PGM salt comprises a PGM organic salt.

7. The chemochromic $H_2$ sensor of claim 1, wherein said PGM compound comprises said PGM complex.

8. The chemochromic $H_2$ sensor of claim 1, further comprising a gas permeable polymer, wherein said chemochromic $H_2$ sensor comprises a composite layer, and wherein said gas permeable polymer provides a continuous phase that completely encapsulates said supports and said PGM compound.

9. The chemochromic $H_2$ sensor of claim 8, wherein said gas permeable polymer comprises silicone.

10. The chemochromic $H_2$ sensor of claim 9, wherein said chemochromic $H_2$ sensor is translucent when formulated into said gas permeable polymer comprising silicone.

11. The chemochromic $H_2$ sensor of claim 1, further comprising an accelerant or contrast additive selected from the group consisting of $MoO_3$, $(NH_4)_6Mo_7O_{24}$, polyoxometalates that include V, Nb, Ta, Cr, Mo or W.

* * * * *